(12) United States Patent
Wang et al.

(10) Patent No.: US 11,684,318 B2
(45) Date of Patent: Jun. 27, 2023

(54) MONITORING DEVICE

(71) Applicant: SHENZHEN MINDRAY BIO-MEDICAL ELECTRONICS CO., LTD., Shenzhen (CN)

(72) Inventors: Cheng Wang, Shenzhen (CN); Lei Qing, Shenzhen (CN); Jie Qin, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 17/357,926

(22) Filed: Jun. 24, 2021

(65) Prior Publication Data

US 2021/0315529 A1    Oct. 14, 2021

Related U.S. Application Data

(63) Continuation-in-part of application No. PCT/CN2018/123153, filed on Dec. 24, 2018, and a
(Continued)

(51) Int. Cl.
*A61B 5/00* (2006.01)
*G06F 3/0482* (2013.01)
(Continued)

(52) U.S. Cl.
CPC .......... *A61B 5/7435* (2013.01); *G06F 3/0482* (2013.01); *G16H 10/60* (2018.01);
(Continued)

(58) Field of Classification Search
CPC .................................................. G06F 3/04847
See application file for complete search history.

(56) References Cited

U.S. PATENT DOCUMENTS 10,856,750 B2 * 12/2020 Indorf ................. A61B 5/746
2007/0011029 A1 * 1/2007 Benson ................ G16H 40/63
707/999.009
(Continued)

FOREIGN PATENT DOCUMENTS

CN        1926550 A     3/2007
CN        1943505 A     4/2007
(Continued)

OTHER PUBLICATIONS

International Search Report issued in corresponding International Application No. PCT/CN2018/123116, dated Sep. 27, 2019, 4 pages.
(Continued)

*Primary Examiner* — Di Xiao
(74) *Attorney, Agent, or Firm* — Bayes PLLC

(57) ABSTRACT

This disclosure provides a monitoring device, which includes a display configured to display information and a processor. The processor is configured to: display a medical advice setup area in a display interface of the monitoring device at a first moment; and display at least one of criticality level information or medical advice information of a monitored subject in the medical advice setup area at a second moment, where the second moment is later than the first moment. The monitoring device in this disclosure may provide different display interfaces for medical staff; a doctor may first configure the criticality level and medical advice information of a monitored subject on an interface so as to prompt a nurse of information that requires attention and measurements requiring execution, after that the nurse may learn the nursing matters requiring attention, which improves the cooperation efficiency between doctors and nurses.

5 Claims, 13 Drawing Sheets

--- display a medical advice setup area in a display interface of a monitoring device at a first moment — 201 display criticality level information and/or medical advice information of a monitored subject in the medical advice setup area at a second moment, where the second moment is later than the first moment — 202

Related U.S. Application Data continuation-in-part of application No. PCT/CN2018/123116, filed on Dec. 24, 2018.

(51) Int. Cl.
*G16H 15/00* (2018.01)
*G16H 40/20* (2018.01)
*G16H 10/60* (2018.01)
*G16H 40/63* (2018.01)
*G06F 3/04817* (2022.01)

(52) U.S. Cl.
CPC ............. *G16H 15/00* (2018.01); *G16H 40/20* (2018.01); *G16H 40/63* (2018.01); *A61B 5/7475* (2013.01); *G06F 3/04817* (2013.01)

(56) References Cited

U.S. PATENT DOCUMENTS

| | | | |
|---|---|---|---|
| 2012/0323086 A1* | 12/2012 | Hansen | A61B 5/7475 600/300 |
| 2013/0044111 A1* | 2/2013 | VanGilder | A61B 5/743 345/440 |
| 2013/0190581 A1* | 7/2013 | Al-Ali | A61B 5/0205 600/324 |
| 2014/0200921 A1 | 7/2014 | Hamill et al. | |
| 2014/0275819 A1 | 9/2014 | Kassem et al. | |
| 2016/0140307 A1* | 5/2016 | Brosnan | G06Q 10/10 600/509 |
| 2016/0239619 A1* | 8/2016 | Abou-Hawili | G16H 40/20 |
| 2017/0102846 A1* | 4/2017 | Ebler | A61M 1/3666 |
| 2017/0193186 A1* | 7/2017 | Tapadar | G16H 40/67 |

FOREIGN PATENT DOCUMENTS

| | | |
|---|---|---|
| CN | 101061983 A | 10/2007 |
| CN | 103690284 A | 4/2014 |
| CN | 104200129 A | 12/2014 |
| CN | 105005685 A | 10/2015 |
| CN | 105534492 A | 5/2016 |
| CN | 106055876 A | 10/2016 |
| CN | 107847176 A | 3/2018 |
| CN | 108877914 A | 11/2018 |

OTHER PUBLICATIONS

International Search Report issued in corresponding International Application No. PCT/CN2018/123153, dated Sep. 25, 2019, 6 pages.

* cited by examiner

MONITORING DEVICE

CROSS-REFERENCE TO RELATED APPLICATIONS

This application is a continuation-in-part of Patent Cooperation Treaty Application No. PCT/CN2018/123116, filed on Dec. 24, 2018, and a continuation-in-part of Patent Cooperation Treaty Application No. PCT/CN2018/123153, filed on Dec. 24, 2018. These priority applications are hereby incorporated by reference in their entireties.

TECHNICAL FIELD

The disclosure relates to the field of monitoring devices.

BACKGROUND

Conventional patient monitors provide real-time monitoring of physiological sign parameters of patients, alarming, data storage and other functions, and some high-end monitors also provide various auxiliary interfaces or functions according to different analysis and viewing requirements of doctors or nurses on patient data.

At present, the monitors on the market each provide real-time parameter and waveform information of a patient on a main interface. When needing to comprehensively analyze or view the condition of a patient, a doctor or a nurse needs to find the functions needed thereby from numerous monitor functions through menu operation according to his/her needs, and sets desired information presentation according to the changes of patients and his/her examination requirements.

Although monitoring information and functions are relatively comprehensive, different departments and different users (such as doctors and nurses) need to perform a large number of operations and setups to get their desired information during use in different work flows or scenarios, so that it is inconvenient to use.

SUMMARY

According to a first aspect of the disclosure, the disclosure provides a monitoring device-based interface display method, including:

Displaying a medical advice setup area in a display interface of a monitoring device at a first moment; and displaying criticality level information and/or medical advice information of a monitored subject in the medical advice setup area at a second moment, where the second moment is later than the first moment.

According to a second aspect of the disclosure, the disclosure provides a monitoring device, including:

a display configured to display information; and
a processor configured to:
display a medical advice setup area in a display interface of a monitoring device at a first moment; and displaying criticality level information and/or medical advice information of a monitored subject in the medical advice setup area at a second moment, where the second moment is later than the first moment.

According to a third aspect of the disclosure, the disclosure provides a monitoring device-based interface display method, including:

displaying a medical advice setup area in a display interface of the monitoring device;
acquiring a first operation instruction; and
displaying criticality level information and/or medical advice information of a monitored subject in the medical advice setup area in response to the first operation instruction.

According to a fourth aspect of the disclosure, the disclosure provides a monitoring device, including:

a display configured to display information; and
a processor configured to:
acquire a first operation instruction; and
display criticality level information and/or medical advice information of a monitored subject in the medical advice setup area in response to the first operation instruction.

DETAILED DESCRIPTION

The following clearly and completely describes the technical solutions in the embodiments of the disclosure with reference to accompanying drawings in the embodiments of the disclosure. Apparently, the described embodiments are merely some rather than all of the embodiments of the disclosure. All the other embodiments obtained by those skilled in the art based on the embodiments of the disclosure without involving any creative efforts shall fall within the scope of protection of the disclosure.

The terms "first", "second", "third", "fourth", etc. (if any) in the specification and the claims of the disclosure and the above-mentioned drawings are used to distinguish similar objects and are not necessarily used to describe a specific order or sequence. It should be understood that the terms used as such may be interchangeable where appropriate, such that the embodiments described herein can be implemented in an order other than what is illustrated or described herein. In addition, the terms "comprise" and "have" and any variations thereof are intended to cover non-exclusive inclusion. For example, a process, method, system, product, or device that comprises a series of steps or units is not necessarily limited to those steps or units explicitly listed, but may comprise other steps or units that are not explicitly listed or are inherent to these processes, methods, products, or devices.

The monitoring devices mentioned in the embodiments of the disclosure are not limited to monitors, and may also be invasive/noninvasive ventilators, anesthesia machines, nurse stations, central stations and other devices having a monitoring function.

Figure 1A:
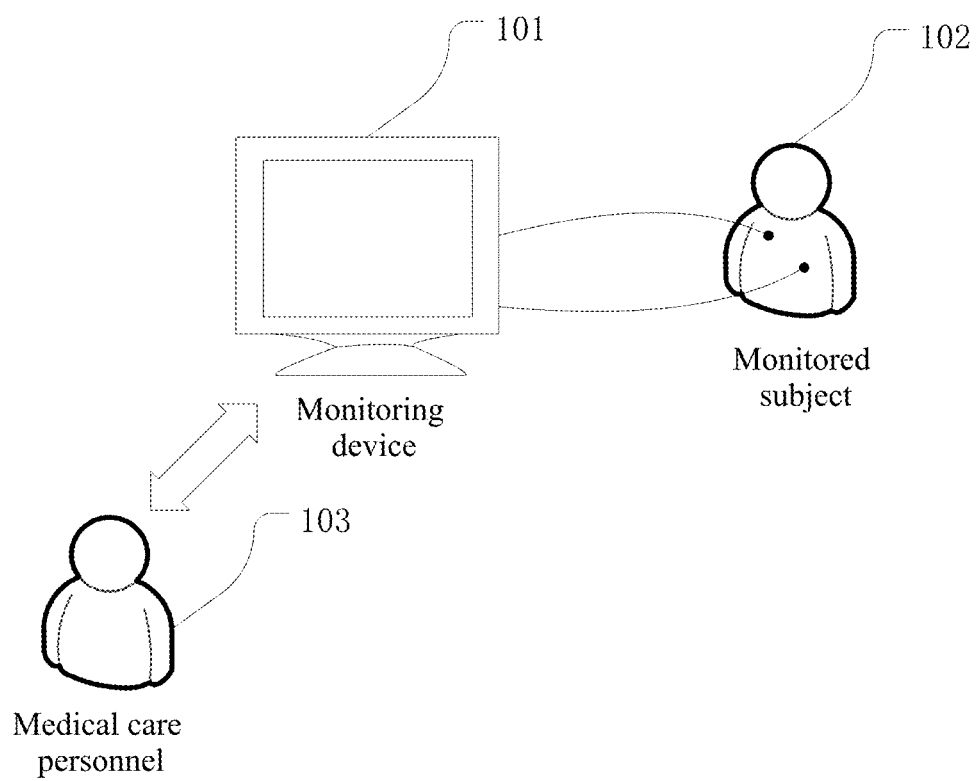
FIG. 1a is a schematic diagram of a medical device-based interface display system in an embodiment of the disclosure.

For ease of understanding, a scenario will be described below in an embodiment of this disclosure, to which a monitoring device-based interface display method is applicable. As shown in FIG. 1a, a monitoring device 101 is connected to a monitored subject 102 via a sensor accessory and used for collecting vital sign parameters of the monitored subject 102. Medical care personnel 103 input related operation instructions on the monitoring device 102, where the operation instructions are used for setting medical advice information and acquiring information relevant to the vital sign parameters. According to the time sequence of the monitored subject from entering into a department, the medical care personnel 103 may input different operation instructions at different moments, such that the monitoring device 101 performs different operations at different moments to help the medical care personnel 103 to carry out better monitoring on the monitored subject 102.

In this disclosure, the monitoring device 101 is a bedside monitor or other devices capable of collecting vital sign parameters. The monitored subject 102 is a patient who needs to be subjected to real-time monitoring of vital sign parameters, The medical care personnel 103 are workers who treat and nurse the patient, such as a doctor, a nurse, a nursing worker, a family member of the patient, etc.

Figure 2:
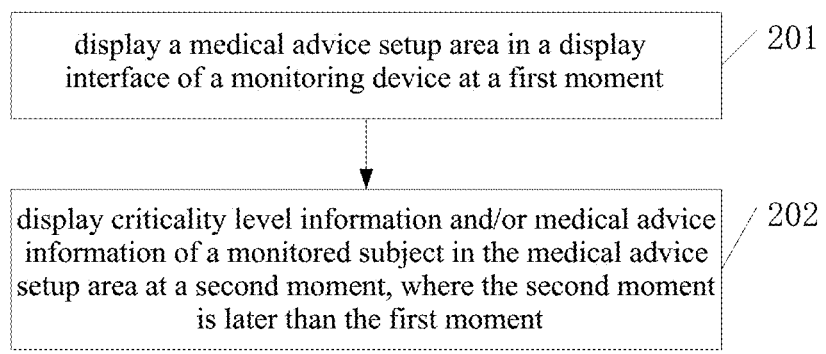
FIG. 2 is a schematic flow chart of a monitoring device-based interface display method in an embodiment of the disclosure.

Based on the above application scenario, the monitoring device-based interface display method in the embodiment of the disclosure will be described below. Referring to FIG. 2, the monitoring device-based interface display method in the embodiment of the disclosure may include the following steps.

At step 201, a medical advice setup area is displayed on a display interface of a monitoring device at a first moment.

Figure 3:
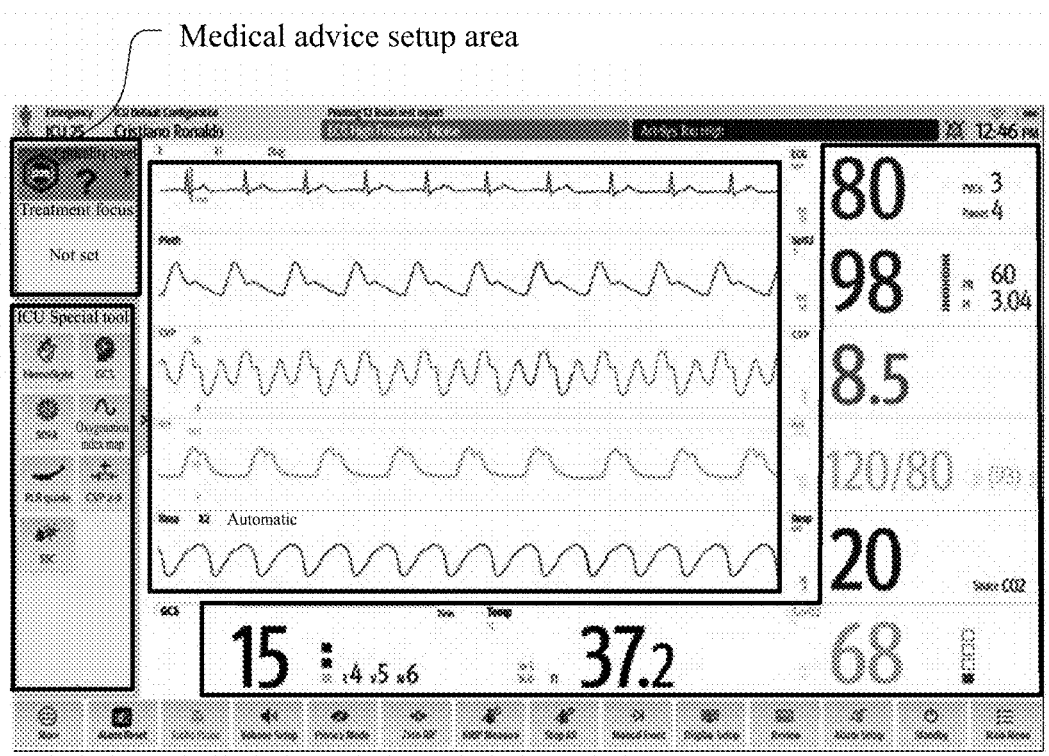
FIG. 3 is a schematic diagram of a medical advice setup area in an embodiment of the disclosure.

Referring to FIG. 3, in this embodiment, at the first moment, the monitoring device may provide a medical advice setup area to the medical care personnel for setting a medical advice. It will be appreciated that the first moment is a moment at which the monitored subject enters into the monitoring department but the medical care personnel do not set a medical advice, and at this moment, the medical advice setup area is a blank display area.

It should be noted that contents presented in the medical advice setup area are different for different medical care personnel, the medical advice setup area is mainly an area presented for a doctor before the medical advice information is set; and the medical advice set by the doctor can be presented in the medical advice setup area after the doctor completes the setup of the medical advice information, and then, the medical advice setup area is mainly an area presented for a nurse and is configured to prompt the nurse to perform a related monitoring task according to the medical advice set by the doctor.

Optionally, the monitoring device may determine whether the user is a doctor or a nurse by scanning an identity of the user, and may further present the medical advice setup area before the medical advice has been set for the doctor or present the medical advice setup area after the medical advice has been set for the nurse.

Optionally, since the medical advice setup areas respectively presented for the doctor and the nurse are different, the monitoring device may identify operation gestures to determine the presented medical advice setup area. For example, if the operation gesture is a swipe trajectory L, the monitoring device may present the medical advice setup area corresponding to the doctor, and if the operation gesture is a swipe trajectory Z, the monitoring device may present the medical advice setup area corresponding to the nurse. In addition, the monitoring device may also switch between the medical advice setup areas corresponding to the doctor and the nurse respectively by identifying a switching gesture, and the switching gesture may be specifically a double-finger swipe gesture. It should be noted that the operation gestures as well as the switching gesture mentioned above are subject to practical disclosures, which will not be limited in detail herein.

Optionally, medical advice setup information may include at least an item of interest to be displayed in a medical advice tool display area. For example, when the user needs to use a pupil measurement tool (a medical advice tool), the user inputs to the medical device the medical advice setup information including setting a pupil measurement icon, and the medical device may display, upon receiving a related instruction, a graphical medical advice tool icon corresponding to the medical advice tool in the medical advice tool display area in response to the instruction, for use by the user. For example, when the medical advice setup information refers to setting the pupil measurement item, the medical device displays a graphical medical advice tool icon for pupil measurement, which corresponds to the pupil measurement item, in the medical advice tool display area on the basis of the medical advice setup information. The user may trigger a relevant function of the pupil measurement tool by triggering the pupil measurement icon.

In this embodiment, in addition to receiving a relevant instruction input by the user, the medical device may also obtain the medical setup information by receiving a system setup instruction. The medical device accesses a medical advice system after responding to the system setup instruction, and acquires the medical advice information from the medical advice system. The graphical medical advice tool icon corresponding to the item of interest is displayed according to the medical advice information, improving the flexibility.

For example, the medical device may automatically acquire a relevant system setup instruction from the medical advice system, and is connected to an external medical advice system according to the system setup instruction, where the external medical advice system includes a bedside monitor, a nurse station, a central station, and other medical advice systems. After being connected to the medical advice system, the medical device acquires medical advice information.

In this embodiment, after receiving a function presentation instruction input by the user, the medical device pops up, in response to the function presentation instruction, a medical advice tool interface which presents the graphical medical advice tool icon corresponding to the function presentation instruction. The medical advice tool interface is popped up and presented on a main monitoring interface, and the specific presentation way includes that the medical advice tool interface may be a window suspended on the main monitoring interface, and the medical advice tool interface covers original information on the main monitoring interface in this case; or the medical advice tool interface may also be an independent presentation area embedded in the main monitoring interface, and the medical advice tool interface does not cover the original information on the main monitoring interface in this case.

At step 202, criticality level information and/or medical advice information of the monitored subject is displayed in the medical advice setup area at the second moment, where the second moment is later than the first moment.

In this embodiment, at the second moment after the first moment, the monitoring device may display the criticality level information of the monitored subject, the medical advice information, or both the criticality level information and the medical advice information in the medical advice setup area. It will be appreciated that this second moment is a moment at which the medical care personnel complete the medical advice setup in the medical advice setup area.

Figure 4:
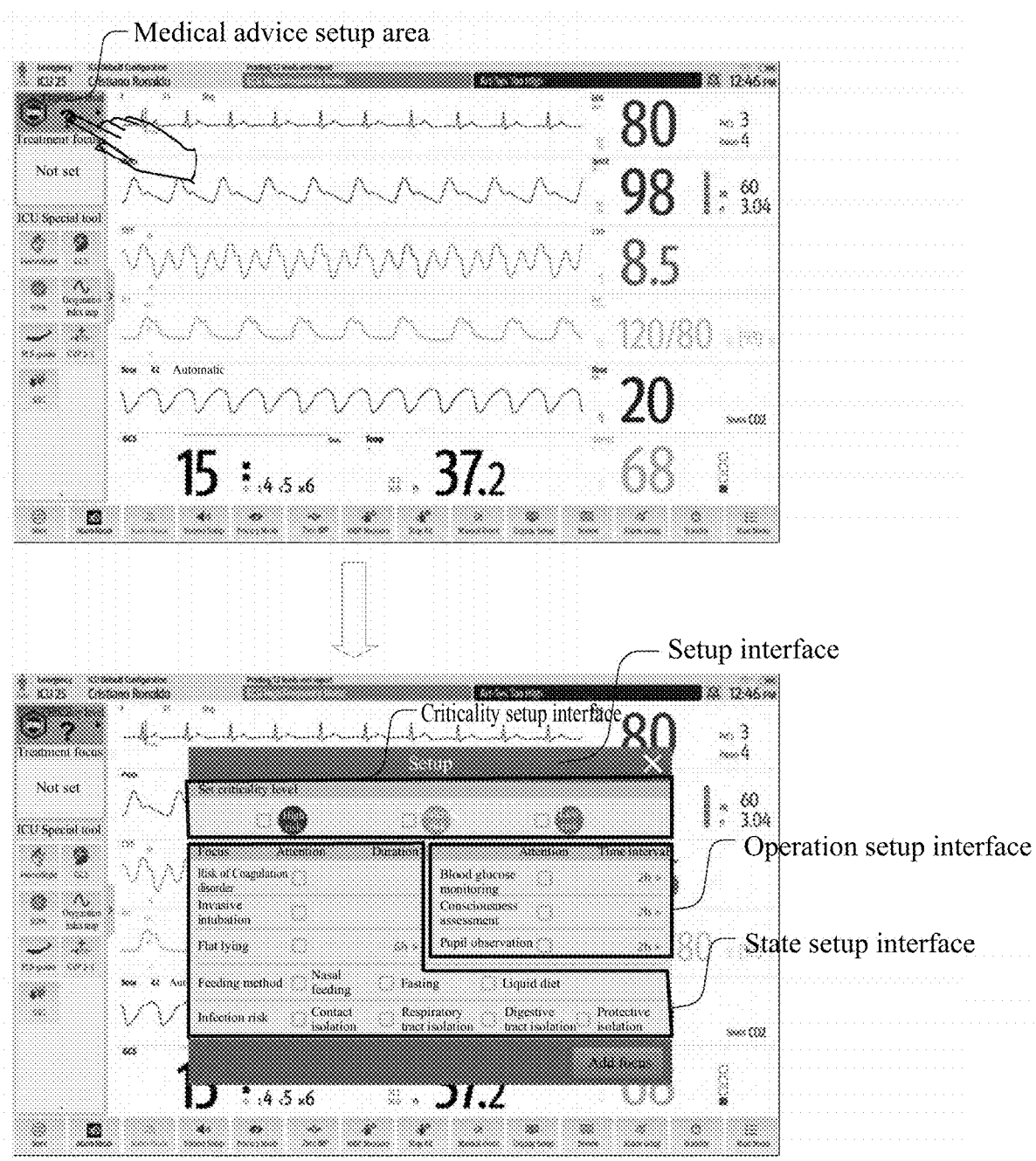
FIG. 4 is a schematic diagram of triggering and displaying a setup interface in an embodiment of the disclosure.

Specifically, referring to FIG. 4, after the first moment and before the second moment, the monitoring device may receive a display setup instruction input by the medical care personnel, then display a setup interface in the form of a pop-up window on the display interface in response to the display setup instruction, and in turn receive the criticality level information and/or the medical advice information input by the medical care personnel on the setup interface, For example, the medical care personnel may perform an operation of ticking or filling in relevant information in the setup interface of the pop-up window as shown in FIG. 4.

Figure 5:
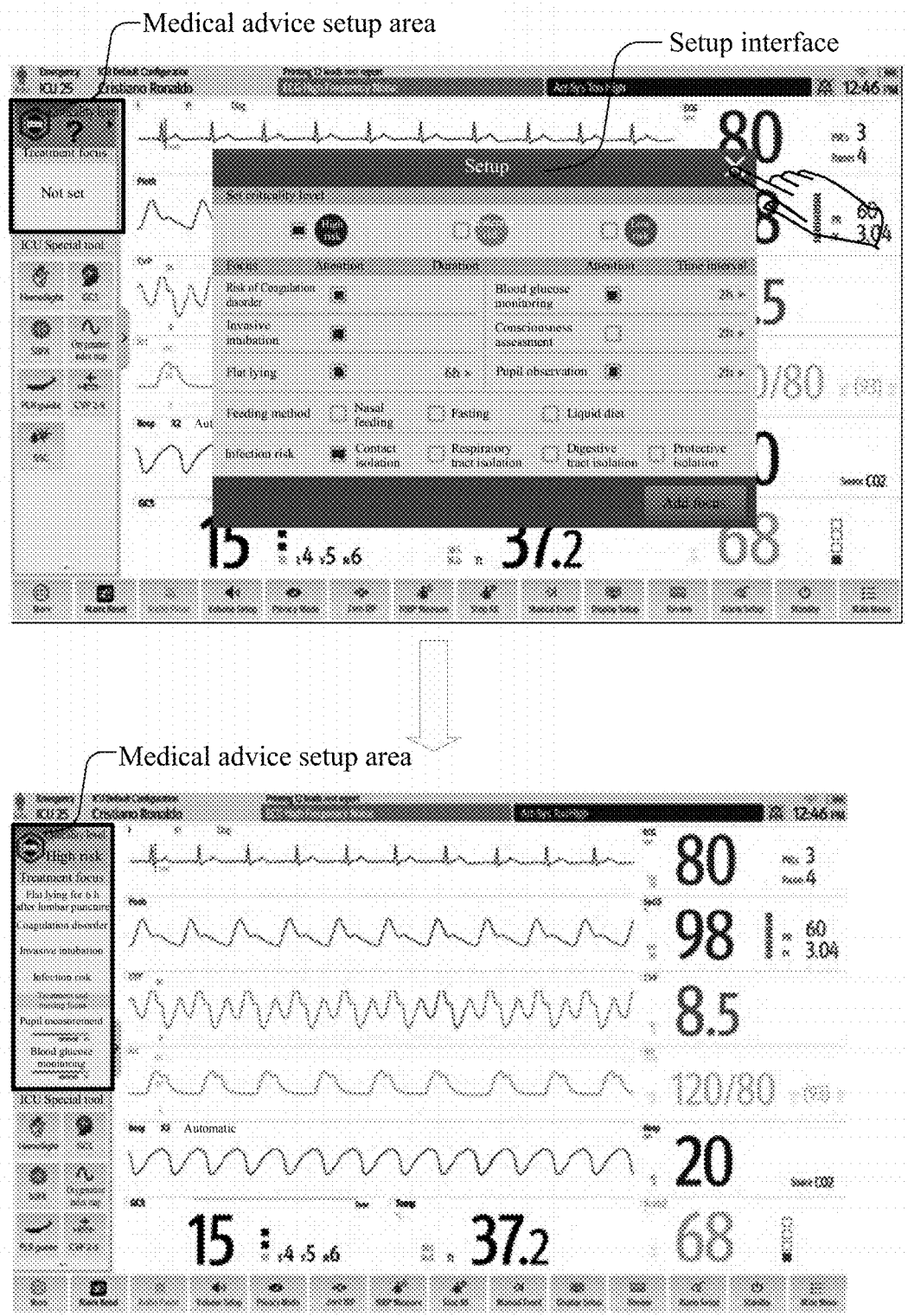
FIG. 5 is a schematic diagram of setting medical advice information and criticality level information in an embodiment of the disclosure.

Referring to FIG. 5, the doctor may manually close the setup interface after completing the medical advice setup in the setup interface of the pop-up window, and the monitoring device further displays the criticality level information and/or the medical advice information set by the doctor in the medical advice setup area. The criticality level information includes a selection result of the doctor on a criticality setup interface. The medical advice information may include at least one of, for example, a selection result of the doctor on a state setup interface, patient information to be of interest that is input by the doctor on the state setup interface, a selection result of the doctor on an operation setup interface, or an operation prompt to be executed by the nurse that is input by the doctor on an operation interface.

Optionally, the setup interface may include at least one of the criticality setup interface, the state setup interface or the operation setup interface, where the criticality setup interface includes at least two criticality level options; the state setup interface includes at least one of a blood coagulation disorder option, an invasive intubation option, a postoperative flat lying option, or an infection risk option; and the operation setup interface includes at least one of operation options of blood glucose monitoring, consciousness evaluation, blood gas analysis, or pupil observation. It should be noted that the information filled by the doctor in the criticality setup interface is mainly used for reflecting the overall state evaluation of the monitored subject, the information filled by the doctor in the state setup interface is mainly used for prompting the nurse of matters that need to be paid attention to in the daily monitoring process, and the information filled by the doctor in the operation setup interface is mainly used for prompting the nurse of data that needs to be monitored.

It should be noted that the criticality level options may be graded into three levels: high risk, moderate risk and low risk. In addition, more levels or scoring manners may also be used. For example, the criticality level options may also be graded into critical and general levels, or the criticality level interface may include more than three options, or the criticality level interface may include a score entering area.

It should be noted that the options on the state setup interface and the operation setup interface may be defined by the user, and the options in the state setup interface and the operation setup interface may be in other forms different from the above examples in practical disclosures, which will not be limited in detail herein.

Optionally, at the second moment, the monitoring device may display the graphical medical advice tool icon corresponding to the item of interest in a flashing manner, and may also display timing information in the medical advice setup area. For example, based on a measurement time set by the doctor in the medical advice information, the monitoring device may set a timing prompt in the medical advice setup area, and when the measurement time is up, the monitoring device may give a prompt in a visual and/or an audio manner, such that the nurse can complete a measurement operation and enter measurement information on time.

In the embodiment, the corresponding item of interest is timed according to the medical advice setup information, and corresponding prompt information is generated after the timing is finished. The prompt information includes: displaying the corresponding graphical medical advice tool icon in a flashing manner. In addition to displaying the corresponding graphical medical advice tool icon in a flashing manner, the prompt information may also include triggering a sounding device to prompt the end of timing in a ringing manner, where the sounding device may be disposed inside the medical device or may be connected to the medical device in a wired or wireless manner, which will not be limited herein. The specific prompt information is set by the user according to his/her own demands.

The medical device receives a timing start instruction triggered by the user from an input device via an input interface circuit 122, where the input device may be a display 119 with a touch function, and the timing start instruction includes an instruction for instructing the medical device to start a timing function corresponding to the graphical medical advice tool icon and a preset time value. After receiving the timing start instruction, the medical device sets a time of the timing function corresponding to the graphical medical advice tool icon according to the timing start instruction and starts the timing function, where a time progress of current timing may be displayed on the corresponding graphical medical advice tool icon. It should be noted that the time progress may also be displayed in the background, which will not be limited herein.

In this embodiment, the monitoring device may display the medical advice setup area in the display interface at the first moment, and the monitoring device may display the criticality level information and/or the medical advice information of the monitored subject in the medical advice setup area at the second moment. As described above, at different moments, the monitoring device may provide different display interfaces for medical care personnel, such that the doctor may first set the criticality level and the medical advice information of the monitored subject in an interface so as to prompt the nurse of information that needs to be paid attention to and measurements that need to be executed, and the nurse then may learn nursing matters that need to be paid attention to by means of an interface, thereby improving the cooperation efficiency between the doctor and the nurse.

It should be noted that at a third moment after the second moment, the monitoring device may also display physiological state information of the monitored subject associated with the criticality level information and/or the medical advice information.

Figure 6:
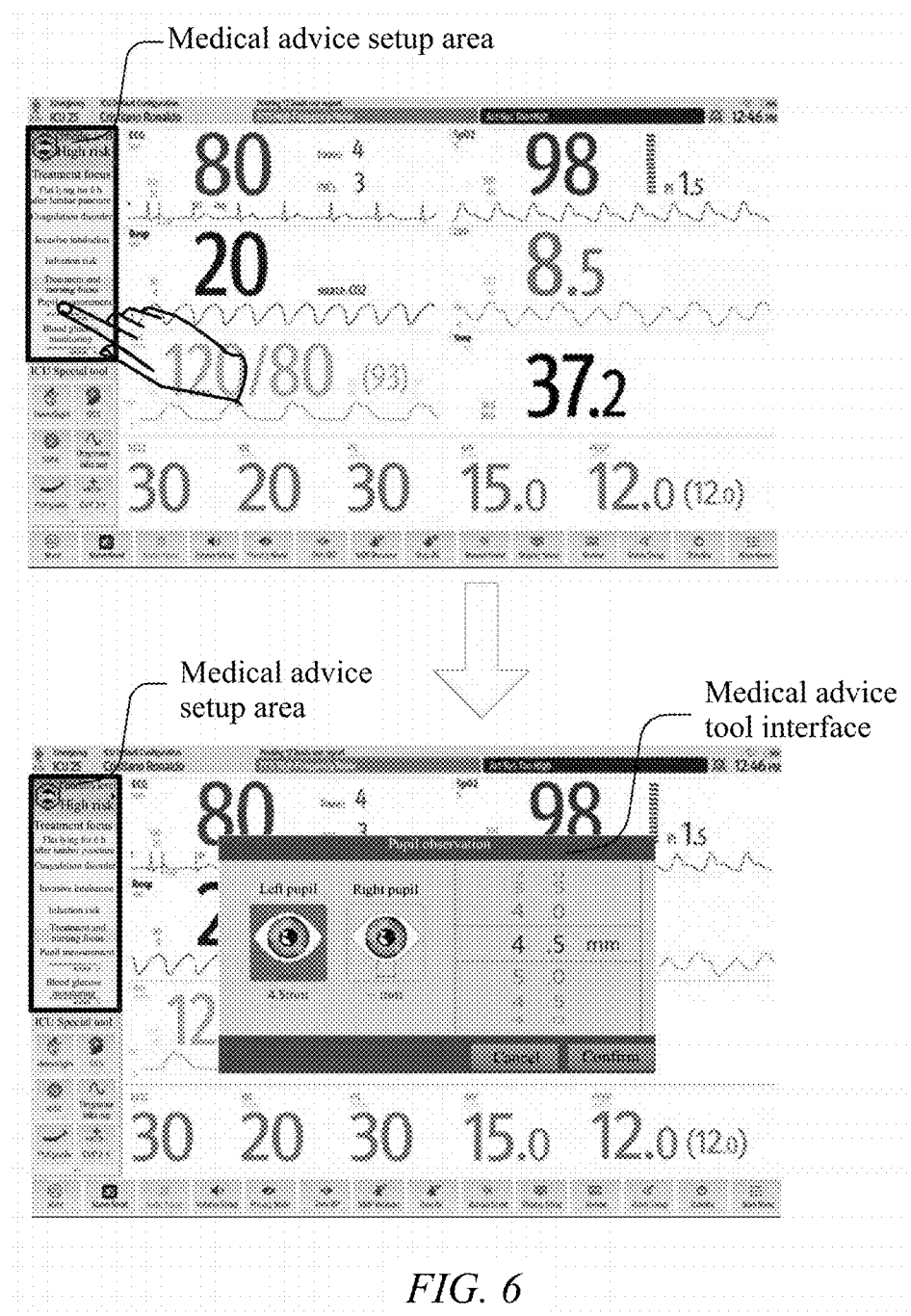
FIG. 6 is a schematic diagram of triggering a medical advice tool interface in an embodiment of the disclosure.

Specifically, referring to FIG. 6, the monitoring device may receive a function display instruction input by the medical care personnel in the medical advice setup area, then display the medical advice tool interface in the form of a pop-up window on the display interface in response to the function display instruction, and in turn receive physiological state information of the monitored subject input by the medical care personnel on the medical advice tool interface, where the physiological state information includes monitoring information of at least one physiological parameter indicated by the criticality level information and/or the medical advice information.

It will be appreciated that the medical care personnel who input the function display instruction and the physiological state information of the monitored subject are usually nurses, the third moment is generally a time for the ward round of the doctor, and the monitoring device displays the physiological state information of the monitored subject associated with the criticality level information and/or the medical advice information for allowing the doctor to learn the real-time physiological state of the monitored subject during ward round.

Optionally, the medical advice tool interface may include at least one of an operation standard, an operation mode or an information entry prompt, where the operation standard is used for indicating requirements to a nurse for a medical operation on the monitored subject, the operation mode is used for indicating steps of the medical operation performed on the monitored subject by the nurse, and the information entry prompt is used for prompting the nurse to input the measurement information associated with the monitored subject. For example, the medical advice tool interface in FIG. 6 displays the information entry prompt, that is, prompting the user to input pupil measurement information of the monitored subject. As another example, the medical advice tool interface displays the operation standard which may instruct the nurse to pay attention to that the monitored subject needs to lie flat for 6 hours postoperatively during monitoring, or to periodically checking whether the tubing of the intubated patient is normal, etc.

Optionally, in addition to the monitoring information of the at least one physiological parameter indicated by the criticality level information and/or the medical advice information, the physiological state information of the monitored subject may include basic physiological parameter information of the monitored subject. That is, the physiological state information of the monitored subject may be monitoring data acquired by the monitoring device by means of a sensor connected to the human body, or monitoring data manually inputted by the nurse.

In this embodiment, the medical device displays the medical advice tool interface corresponding to the graphical medical advice tool icon according to the function display instruction input by the user, and the medical advice tool interface may display the operation standard information for indicating the requirements to the user for the medical operation on the monitored subject, the operation mode information for indicating the steps of the medical operation performed on the monitored subject by the user, and the information entry prompt for prompting the user to input the measurement information associated with the monitored subject. The operation standard information, the operation mode information and the information entry prompt may either be displayed simultaneously or separately.

In the case where the operation standard information, the operation mode information and the information entry prompt are separately displayed: after the user inputs the function display instruction by means of the graphical medical advice tool icon, a secondary menu containing the operation standard information, the operation mode information and the information entry prompt may be displayed in the medical advice tool interface corresponding to the graphical medical advice tool icon, where the secondary tool icon menu may be options corresponding to texts or options corresponding to graphical icons, which will not be limited herein. The medical device receives instructions input by the user by means of the options in the secondary menu and displays the corresponding information. For example, after the user selects the option corresponding to the operation standard information, the operation standard information for indicating the requirements to the user for the medical operation on the monitored subject is displayed in the medical advice tool interface.

It should be noted that when the operation standard information, the operation mode information and the information entry prompt are separately displayed, one or more kinds of those information may be displayed, which will not be limited herein.

In an embodiment of the disclosure, after receiving the function display instruction input by the user, the medical device displays, in response to the function display instruction, the operation standard information for indicating the requirements to the user for the medical operation on the monitored subject; and/or the medical device displays the operation mode information for indicating the steps of the medical operation performed on the monitored subject by the user in the medical advice tool interface; and/or the medical device displays the information entry prompt for prompting the user to input the measurement information associated with the monitored subject in the medical advice tool interface. By displaying multiple kinds of information and/or the information entry prompt in the medical advice tool interface, the convenience of the user in using the medical advice tools is further improved. The feasibility of the solution of this disclosure is improved.

In an embodiment of the disclosure, after receiving the measurement information input by the user through an information input box of the medical advice tool interface, the medical device may store the measurement information. The measurement information is obtained by measuring the monitored subject by the user and includes a measurement result corresponding to at least one measurement item in the items of interest corresponding to the graphical medical advice tool icon, thereby improving the feasibility of the solution of this disclosure.

Figure 7:
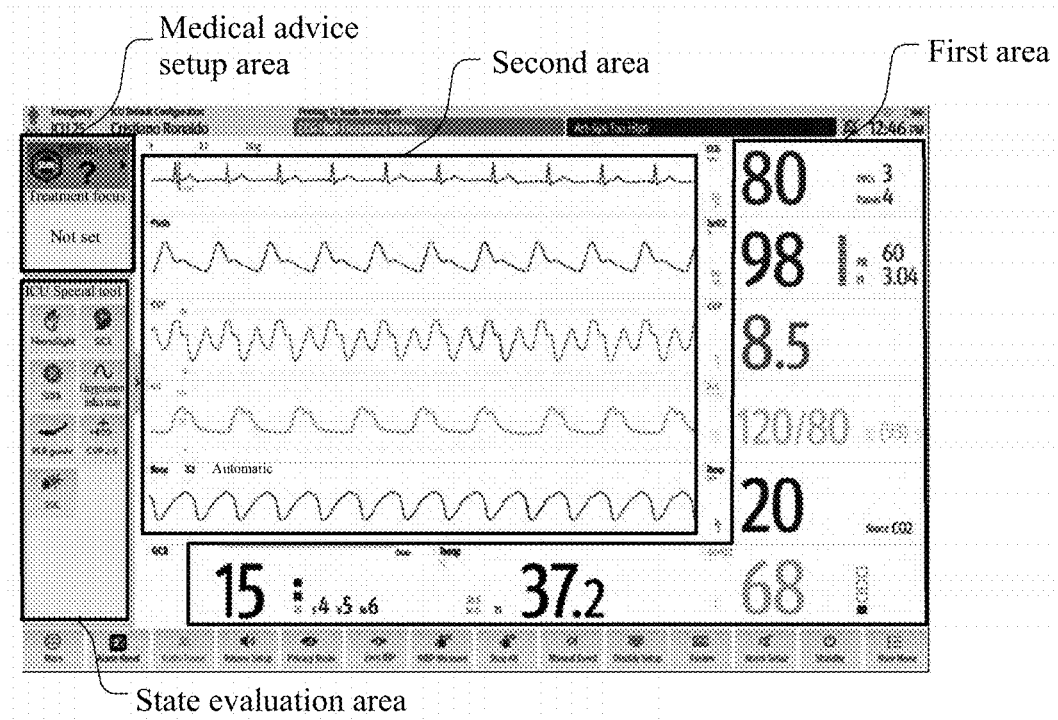
FIG. 7 is a schematic diagram of a state interface in an embodiment of the disclosure.

Referring to FIG. 7, the basic physiological parameter information of the monitored subject may be displayed in a state interface as shown in FIG. 7. It will be appreciated that when the monitored subject is transferred to a department of which a doctor is in charge and is initially connected to a sensor accessory, that is, at the first moment, the monitoring device may display the state interface. For example, a patient A was originally in the department of cardiology, but due to the aggravation of the disease, his/her life is in danger at any time, and the patient needs to be transferred to an Intensive Care Unit (ICU) for 24-hour observation. When the patient A is transferred to the ICU, a doctor in the ICU department needs to evaluate the state of the patient and connect a sensor accessory of a monitor to the heart, fingers and other parts of the body of the patient A, and the monitoring device displays the state interface in this case.

The state interface further includes a first area, a second area and a state evaluation area in addition to the medical advice setup area, where the first area is used for displaying real-time values of vital sign parameters collected by the monitoring device when the monitored subject is initially connected to the sensor accessory, the second area is used for displaying waveforms of the vital sign parameters collected by the monitoring device when the monitored subject is initially connected to the sensor accessory, and the state evaluation area includes an entry of at least one evaluation tool or an analysis tool for a doctor to evaluate the state of a tested subject. It can be seen that the first area and the second area may display the basic physiological parameter information of the monitored subject, and the first area and the second area update the basic physiological parameter information of the monitored subject in real time over time. In addition, for two different roles of the doctor and the nurse, specific display modes of the monitoring device in the corresponding areas may be different. For example, the real-time values are displayed in the form of normal fonts in the first area and the real-time waveforms are displayed in the second area of an interface presented for the doctor, and the real-time values are displayed in the form of larger fonts in the first area of an interface presented for the nurse.

Figure 8:
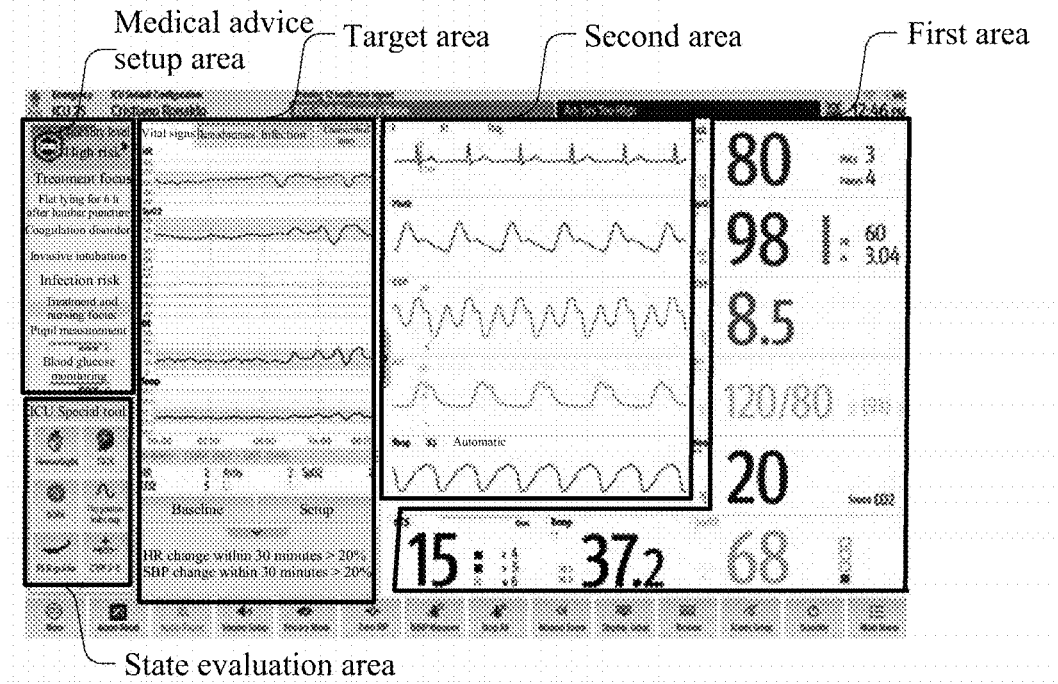
FIG. 8 is a schematic diagram of an interface displaying physiological state information of a monitored subject in an embodiment of the disclosure.

Optionally, referring to FIG. 8, the monitoring device may display a target area in which the monitoring information of at least one physiological parameter indicated by the criticality level information and/or the medical advice information is displayed. Optionally, the monitoring device displays the monitoring information of the at least one physiological parameter indicated by the medical advice information in the form of an analog waveform and/or a trend chart in the target area, where the analog waveform and/or the trend chart may be generated according to the values of the physiological sign parameters collected in the last 8 hours, according to the values of the physiological sign parameters collected within the last 24 hours, or according to the physiological sign parameters collected within other periods of time, which will not be limited in detail herein.

It should be noted that if the medical advice information set by the doctor is too much to be completely displayed in the medical advice setup interface, the nurse may view the complete medical advice information in the medical advice tool interface by means of scrolling or paging. In addition, after the nurse views the medical advice information, if the medical advice only prompts the nurse of the matters that need to be paid attention to in the daily monitoring process without instructing the nurse to feed back the monitoring data, the nurse may not execute the operation of inputting the monitoring data.

As described above, the monitoring device may display the medical advice information and/or the criticality level information set by the doctor to prompt the nurse, and may also display the physiological state information of the monitored subject input by the nurse and associated with the medical advice information and/or the criticality level information, thereby making the doctor conveniently learn the latest disease state of the monitored subject in real time during ward round, and further improving the cooperation efficiency between the doctor and the nurse.

In this embodiment, after receiving the measurement information or ward-round information input by the user through the information input box, the medical device may send the measurement information or the ward-round information to an external device in a wired and/or wireless transmission manner or in other manners, where the external device includes a nurse station, a central station, a mobile terminal, a clinical information system and an electronic medical record system, and the measurement information further includes the measurement information monitored by the medical device itself, which will not be limited herein.

Figure 1B:
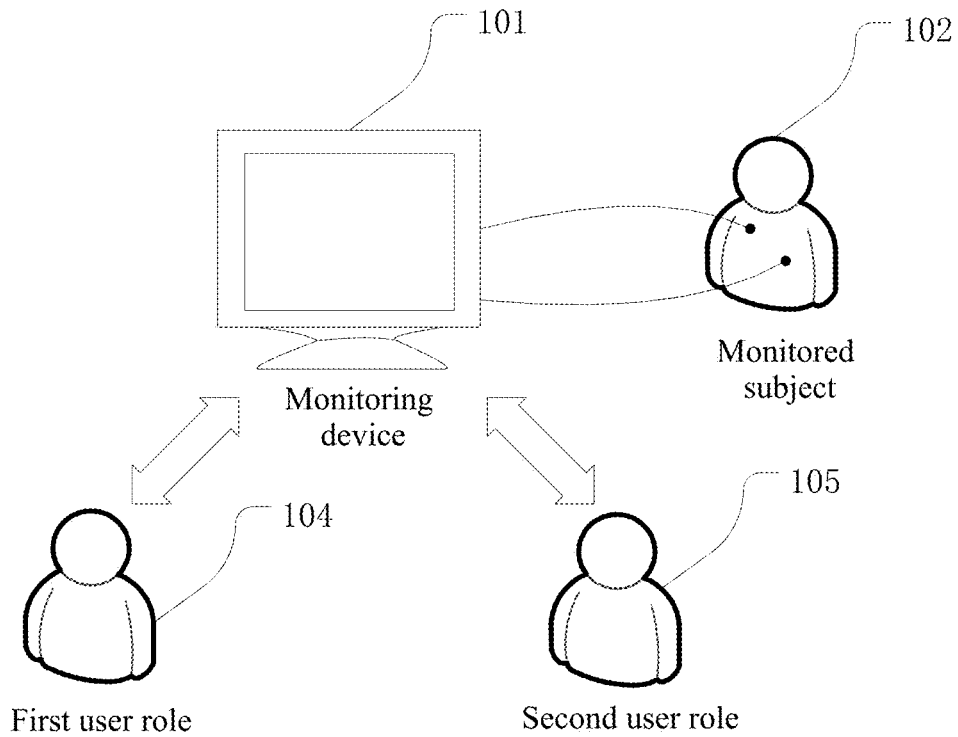
FIG. 1b is another schematic diagram of a medical device-based interface display system in an embodiment of the disclosure.

As shown in FIG. 1b, the monitoring device 101 is connected to the monitored subject 102 via the sensor accessory and used for collecting vital sign parameters of the monitored subject 102. A first user role 104 and a second user role 105 are used for inputting related operation instructions on the monitoring device 102 so as to acquire information associated with the vital sign parameters, where the information to be acquired is different due to the difference of the first user role 104 and the second user role 105. The monitoring device 102 may identify users with different roles to display to a role the information that needs to be acquired thereby on a monitoring interface corresponding to the role.

In this embodiment, the monitoring device 101 is a bedside monitor or other devices capable of collecting the vital sign parameters; the monitored subject 102 is also a patient who needs to be subjected to real-time monitoring of the vital sign parameters; and the first user role 104 and the second user role 105 are workers who treat and nurse the patient, such as a doctor, a nurse, a nursing worker, a family member of the patient, etc. The following embodiment will be described as an example, with the first user role 104 as a doctor and the second user role as a nurse.

Figure 9:
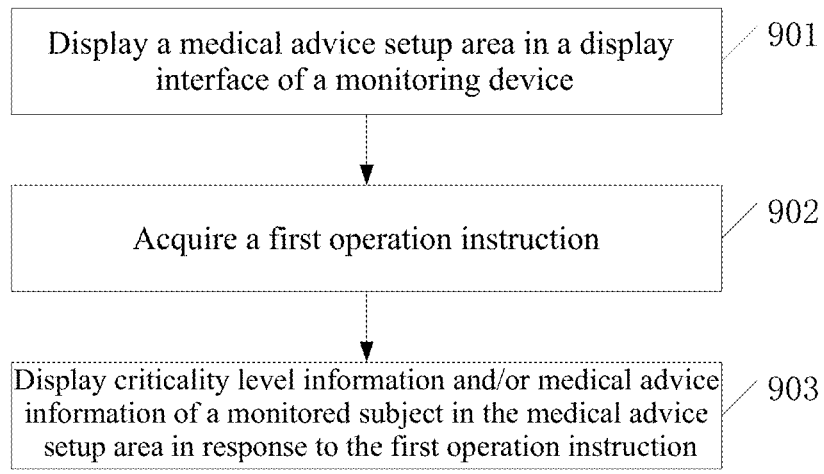
FIG. 9 is a schematic flow chart of another monitoring device-based interface display method in an embodiment of the disclosure.

Based on the above application scenario, the monitoring device-based interface display method in the embodiment of the disclosure will be described below. Referring to FIG. 9, the monitoring device-based interface display method in the embodiment of the disclosure includes the following steps.

At step 901, a medical advice setup area is displayed on a display interface of a monitoring device.

Referring to FIG. 3, in this embodiment, the monitoring device may provide a medical advice setup area for setting a medical advice to the doctor. It will be appreciated that when the doctor does not set the medical advice, the medical advice setup area is a blank display area.

At step 902, a first operation instruction is acquired.

In this embodiment, the first operation instruction is an operation instruction input by the doctor, that is, the doctor fills in the medical advice information by inputting the first operation instruction.

Specifically, referring to FIG. 4, the monitoring device may receive a display setup instruction triggered by the doctor in the medical advice setup area, then display a setup interface in the form of a pop-up window on the display interface in response to the display setup instruction, and in turn receive a first operation instruction input by the doctor on the setup interface, where the first operation instruction may be an operation of ticking or filling in the relevant information by the doctor in the setup interface of the pop-up window shown in FIG. 4.

Optionally, the setup interface may include at least one of the criticality setup interface, the state setup interface and the operation setup interface, where the criticality setup interface includes at least two criticality level options; the state setup interface includes at least one of a blood coagulation disorder option, an invasive intubation option, a postoperative flat lying option, or an infection risk option; and the operation setup interface includes at least one of operation options of blood glucose monitoring, consciousness evaluation, blood gas analysis, or pupil observation. It should be noted that the information filled by the doctor in the criticality setup interface is mainly used for reflecting the overall state evaluation of the monitored subject, the information filled by the doctor in the state setup interface is mainly used for prompting the nurse of matters that need to be paid attention to in the daily monitoring process, and the information filled by the doctor in the operation setup interface is mainly used for prompting the nurse of data that needs to be monitored.

It should be noted that the options on the state setup interface and the operation setup interface may be defined by the user, and the options in the state setup interface and the operation setup interface may be in other forms different from the above examples in practical disclosures, which will not be limited in detail herein.

At step 903, in response to the first operation instruction, criticality level information and/or medical advice information of the monitored subject is displayed in the medical advice setup area.

In this embodiment, after the monitoring device acquires the first operation instruction, that is, after the doctor completes the setup of the medical advice, the monitoring device may display the criticality level information of the monitored subject, the medical advice information, or both the criticality level information and the medical advice information in the medical advice setup area.

Specifically, referring to FIG. 5, the doctor may manually close the setup interface after completing the medical advice setup in the setup interface of the pop-up window, and the monitoring device further displays the criticality level information and/or the medical advice information set by the doctor in the medical advice setup area. The criticality level information includes a selection result of the doctor on the criticality setup interface. The medical advice information may include at least one of, for example, a selection result of the doctor on the state setup interface, patient information to be of interest that is input by the doctor on the state setup interface, a selection result of the doctor on the operation setup interface, or an operation prompt to be executed by the nurse that is input by the doctor on an operation interface.

Optionally, the monitoring device may also display timing information in the medical advice setup area. For example, based on a measurement time set by the doctor in the medical advice information, the monitoring device may set a timing prompt in the medical advice setup area. When the measurement time is up, the monitoring device may give a prompt in a visual and/or an audio manner, such that the nurse can complete a measurement operation and enter measurement information on time.

In this embodiment, the monitoring device may display the medical advice setup area, and after acquiring the first operation instruction inputted by the doctor, the monitoring device may display the criticality level information and/or the medical advice information of the monitored subject in the medical advice setup area. As described above, the doctor may set the criticality level and the medical advice information of the monitored subject in an interface so as to prompt a nurse of information that needs to be paid attention to and measurements that need to be executed, and the nurse may learn nursing matters that need to be paid attention to by means of an interface, thereby improving the cooperation efficiency between the doctor and the nurse.

It should be noted that the monitoring device may also display other interfaces in addition to the medical advice setup area displayed on the display interface. In particular, the monitoring device may also display an initial state interface of the monitored subject, and when the monitored subject is transferred to the department of which the doctor is in charge, and is initially connected to the sensor accessory, the monitoring device displays the initial state interface.

Referring to FIG. 7, the interface presented for the doctor and the interface presented for the nurse by the monitoring device may each include a first area, a second area and a state evaluation area. For two different roles of the doctor and the nurse, the specific display modes of the monitoring device in the corresponding areas may be different, for example, the real-time values are displayed in the form of normal fonts in the first area and the real-time waveforms are displayed in the second area of an interface presented for the doctor, and the real-time values are displayed in the form of larger fonts in the first area of an interface presented for the nurse.

Optionally, the monitoring device may acquire a second operation instruction after displaying the criticality level information and/or the medical advice information of the monitored subject in the medical advice setup area. In this embodiment, the second operation instruction is an operation instruction input by the nurse, that is, the nurse further views detailed medical advice information or opens an interface recording the physiological state information of the monitored subject by inputting the second operation instruction.

Specifically, referring to FIG. 6, the monitoring device may receive the second operation instruction triggered by the nurse in the medical advice setup area, and then display the medical advice tool interface in the form of a pop-up window on the display interface in response to the second operation instruction.

Optionally, the medical advice tool interface may include at least one of an operation standard, an operation mode or an information entry prompt, where the operation standard is used for indicating requirements to a nurse for a medical operation on the monitored subject, the operation mode is used for indicating steps of the medical operation performed on the monitored subject by the nurse, and the information entry prompt is used for prompting the nurse to input measurement information associated with the monitored subject. For example, the medical advice tool interface in FIG. 6 displays the information entry prompt, that is, prompting the user to input pupil measurement information of the monitored subject. As another example, the medical advice tool interface displays the operation standard which may instruct the nurse to pay attention to that the monitored subject needs to lie flat for 6 hours postoperatively during monitoring, or to periodically checking whether the tubing of the intubated patient is normal, etc.

Optionally, if the medical advice tool interface displays the information entry prompt as shown in FIG. 7, the monitoring device may also acquire a third operation instruction, which is an instruction for causing the nurse to input the physiological state information of the monitored subject in this embodiment. In response to the third operation instruction, the monitoring device then displays the physiological state information of the monitored subject on the display interface, allowing the doctor to learn the real-time physiological state of the monitored subject during the ward round. The physiological state information may include the physiological parameter information displayed on an initial state interface of the original monitored subject, and may also include the monitoring information of at least one physiological parameter indicated by the criticality level information and/or the medical advice information. It will be understood that the physiological state information of the monitored subject may be monitoring data acquired by the monitoring device by means of the sensor connected to the human body, or monitoring data manually inputted by the nurse.

In particular, referring to FIG. 8, in response to the third operation instruction, the monitoring device may display a target area in which the monitoring information of the at least one physiological parameter indicated by the criticality level information and/or the medical advice information is displayed. Optionally, the monitoring device displays the monitoring information of the at least one physiological parameter indicated by the medical advice information in the form of an analog waveform and/or a trend chart in the target area, where the analog waveform and/or the trend chart may be generated according to the values of the physiological sign parameters collected in the last 8 hours, according to the values of the physiological sign parameters collected within the last 24 hours, or according to the physiological sign parameters collected within other periods of time, which will not be limited in detail herein.

As described above, the monitoring device may display the medical advice information and/or the criticality level information set by the doctor to prompt the nurse, and may also display the physiological state information of the monitored subject input by the nurse and associated with the medical advice information and/or the criticality level information, thereby making the doctor conveniently learn the latest disease state of the monitored subject in real time during ward round, and further improving the cooperation efficiency between the doctor and the nurse.

Optionally, the monitoring device may classify the collected physiological sign parameters into multiple types within the target area. For example, the physiological sign parameters may be classified into several types: basic vital signs (such as heart rate, blood oxygen saturation, non-invasive blood pressure, etc.), hemodynamics (such as heart rate, central venous pressure, systemic vascular resistance index, etc.), infections (such as heart rate, temperature, central venous pressure, central venous blood oxygen saturation, etc.), craniocerebral injuries (such as heart rate, temperature, pupil measurement, etc.), respiratory systems (such as respiratory rate, blood oxygen saturation, end-expiratory CO2 concentration, etc.), and nutritional metabolism (daily energy consumption of patients, etc.).

Optionally, after viewing the physiological state information of the monitored subject fed back by the monitoring device during the ward round, the doctor may further adjust the medical advice information and the criticality level information of the monitored subject in real time. In addition, the monitoring device may send the physiological state information of the monitored subject to an external device, which may include at least one of a central station, a mobile terminal, or a computerized medical record system, such that the doctor may also remotely set the criticality level information and the medical advice information by means of the external device.

The following describes the interfaces that need to be presented by the monitoring device at various time points sequentially from the time that the monitored subject enters into the ICU department. Based on a business process of the IUC department, the interface as shown in FIG. 3 may be displayed when the patient enters into the department. The doctor then needs to evaluate the initial state of the patient, make a preliminary therapeutic scheme and set a medical advice, and the monitoring device may display the interface as shown in FIG. 4 in this case. Thereafter, the patient is in a daily monitoring phase, the nurse is responsible for the patient's nursing, monitoring and recording work at the bedside, and the monitoring device may display the interface as shown in FIG. 6 in this case. The doctor carries out shifting of duty and ward round at the bedside of the patient every morning and evening, and the monitoring device may display the interface as shown in FIG. 8 in this case.

Optionally, this disclosure may further provide another method for presenting the medical advice tool in another embodiment. In this embodiment, monitoring data of at least one physiological sign parameter of a monitored subject is acquired, where the monitoring data is collected by means of a sensor accessory connected to the monitored subject. Corresponding waveform monitoring information is generated based on the monitoring data; and the waveform monitoring information is displayed in a monitoring information display area, where the waveform monitoring information includes at least one of value monitoring information, physiological sign analog signal waveform information, physiological sign trend waveform information or statistical analysis information of trend waveforms.

In this embodiment, a waveform monitoring information display area is generated and displayed on a main monitoring interface, and the waveform monitoring information displayed in the waveform monitoring information display area includes displaying at least one of a first area or a second area, where the first area is used for displaying the value monitoring information, and the second area is used for displaying the physiological sign analog signal waveform information, the physiological sign trend waveform information and the statistical analysis information of trend waveforms.

The value monitoring information includes coma scale scores, body surface temperature data, heart rate values, blood oxygen saturation values and body surface temperature values (including value information displayed in the form of large fonts in the drawings). The physiological sign analog signal waveform information includes electrocardiogram waveforms, blood oxygen plethysmograms (PLETHs), etc. The physiological sign trend waveform information includes a blood oxygen saturation trend chart, an invasive arterial pressure trend chart, a pulse rate trend chart, an intra-cavity and body surface temperature trend chart, a carbon dioxide inhalation volume trend chart, etc. The statistical analysis information of the waveforms includes at least one of the statistical analysis information of long trend waveforms or the statistical analysis information of short trend waveforms.

Figure 11A:
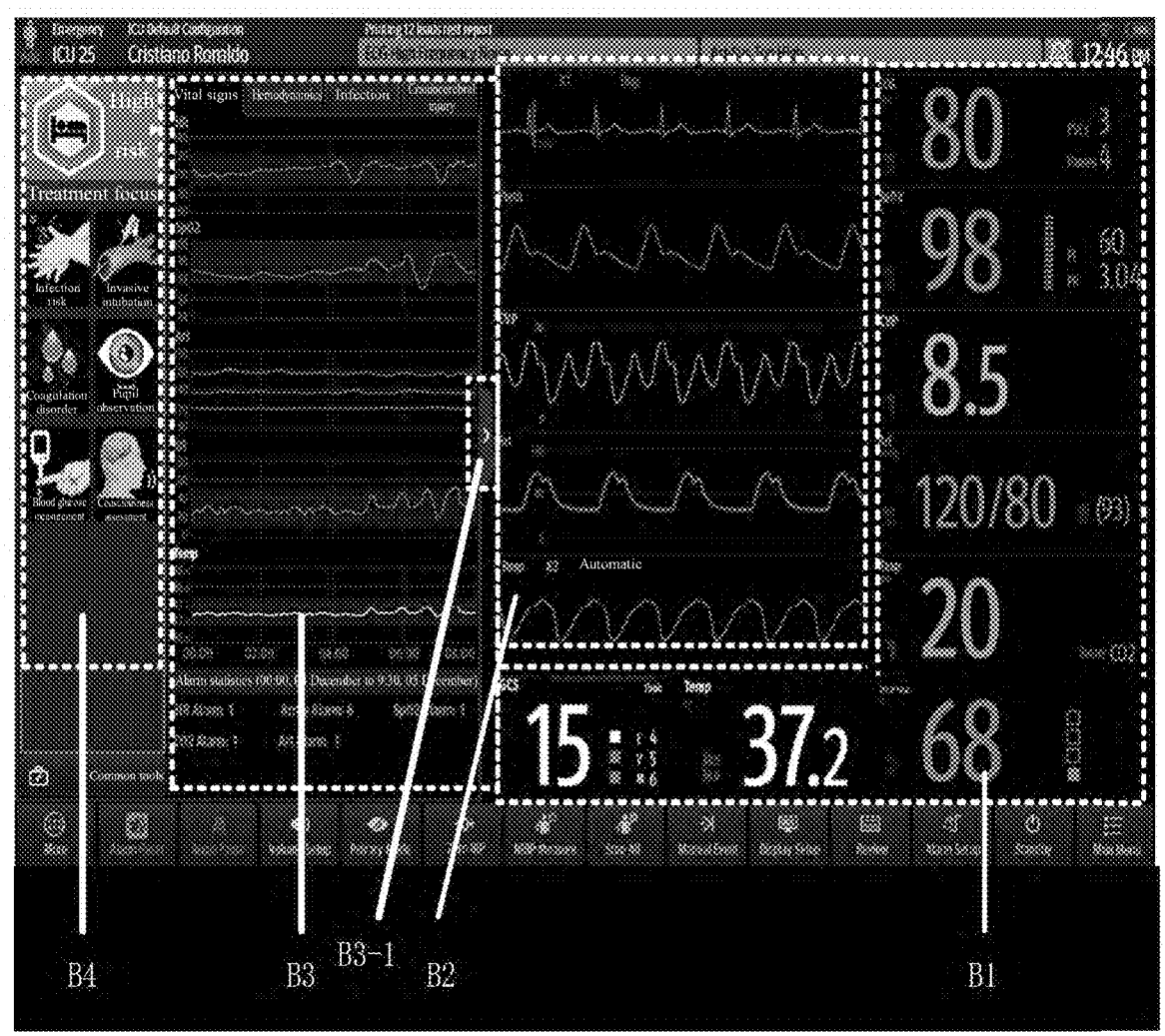
FIG. 11a is a schematic diagram of a main monitoring interface in an embodiment of the disclosure.

For ease of understanding, as shown in FIG. 11a, FIG. 11a is a schematic interface diagram of a main monitoring interface in an embodiment of the disclosure. In FIG. 11a, the information displayed in an area B1 is the value monitoring information, including the coma scale scores, the body surface temperature data, the heart rate values, the blood oxygen saturation values, the body surface temperature values, etc. The information displayed in an area B2 is the physiological sign waveform information (including the physiological sign analog signal waveform information and the physiological sign trend waveform information), including: heart rate (HR) waveforms, blood oxygen saturation (SPO2) waveforms, invasive arterial pressure (ART) waveforms, pulse rate (PR) waveforms, intra-cavity and body surface temperature (TEMP) waveforms, and carbon dioxide inhalation volume waveforms. An area B3 shows the physiological sign trend waveform information and the statistical analysis information of trend waveforms, and an area B4 is a dedicated medical advice tool display area, in which at least one medical advice tool is displayed.

The B3 area in FIG. 11a shows the physiological sign trend waveform information and the statistical analysis information of trend waveforms under a vital sign physiological system option, including the heart rate (HR) waveforms, the blood oxygen saturation (SPO2) waveforms, the invasive arterial pressure (ART) waveforms, the pulse rate (PR) waveforms, the intra-cavity and body surface temperature (TEMP) waveforms and other trend waveform information within 8 hours.

Figure 11B:
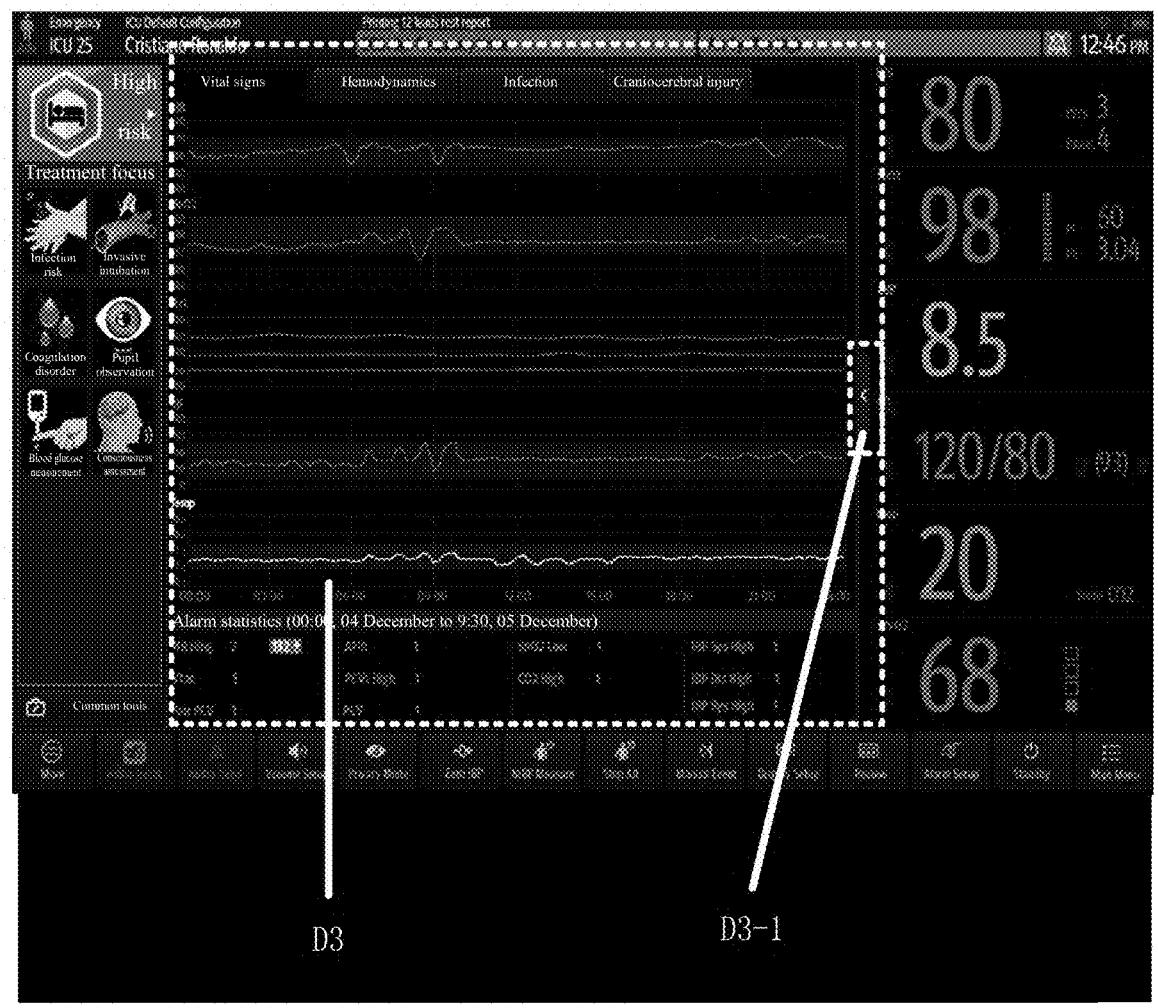
FIG. 11b is another schematic diagram of a main monitoring interface in an embodiment of the disclosure.

The medical device displays the physiological sign trend waveform information and the statistical analysis information of trend waveforms under different physiological system options after receiving operation instructions for triggering options corresponding to different physiological systems by the user. The operation instructions may be operation instructions input by the user by means of a touch display 119 or an external input device, or operation instructions input by the user by triggering other input devices located on the medical device; or operation instructions preset inside the medical device, which are triggered when the running time of the medical device reaches a preset threshold, which will not be limited herein. For example, when the user wants to further learn the more detailed physiological sign trend waveform information and the statistical analysis information of trend waveforms under a vital sign option, the user may click an arrow icon in an area B3-1 in the area B3 by means of the display 119, and the medical device displays the more detailed physiological sign trend waveform information and the statistical analysis information of trend waveforms over a longer period of time under the current vital sign option after receiving an operation instruction from the user. For ease of understanding, as shown in FIG. 11b, FIG. 11b is another schematic diagram of a main monitoring interface in an embodiment of the disclosure. In the FIG. 11b, the medical device displays the more detailed physiological sign trend waveform information and the statistical analysis information of trend waveforms under a vital sign system option after receiving an operation instruction from the user, and the physiological sign trend waveform information and the statistical analysis information of trend waveforms associated with the monitored subject within 24 hours are displayed in an area D3, where statistical alarm information in the area D3 is statistical analysis information of the trend waveforms within a period of time. For example, if the blood oxygen saturation (SPO2) is lower or higher than a certain normal threshold within a period of time, the medical device records the event that the blood oxygen saturation exceeds the normal threshold value. In the scenario shown in FIG. 11b, when needing to display the physiological sign trend waveform information and the statistical analysis information of trend waveforms within 8 hours, the user may click an arrow icon in an area D3-1, and the medical device displays the physiological sign trend waveform information and the statistical analysis information of trend waveforms within 8 hours after receiving the operation instruction from the user.

Figure 11C:
FIG. 11c is another schematic diagram of a main monitoring interface in an embodiment of the disclosure.
Figure 11D:
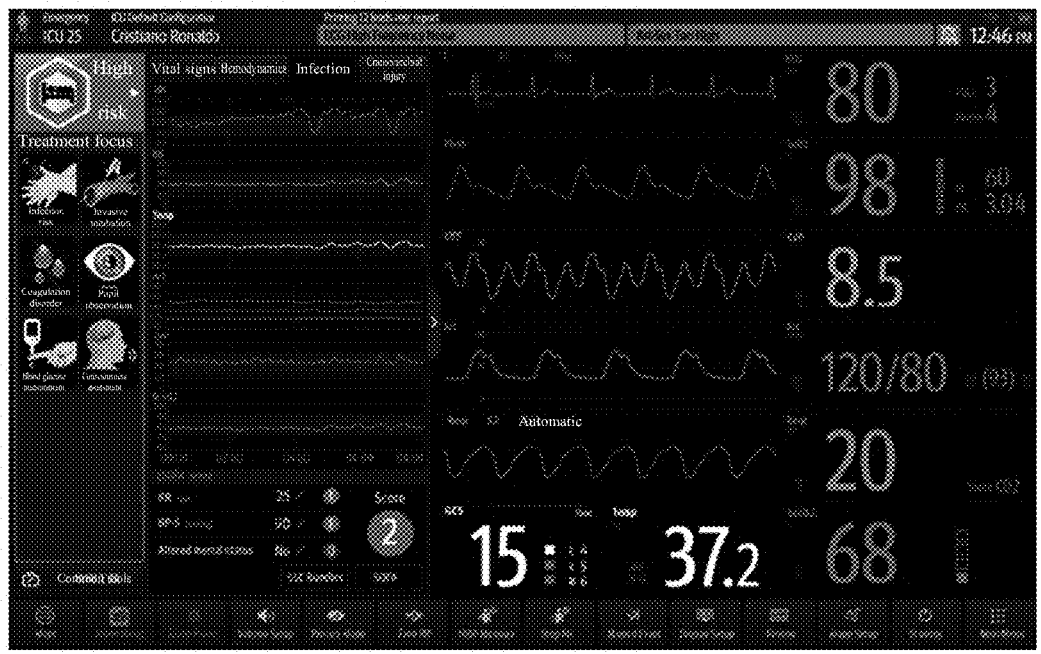
FIG. 11d is another schematic diagram of a main monitoring interface in an embodiment of the disclosure.
Figure 11E:
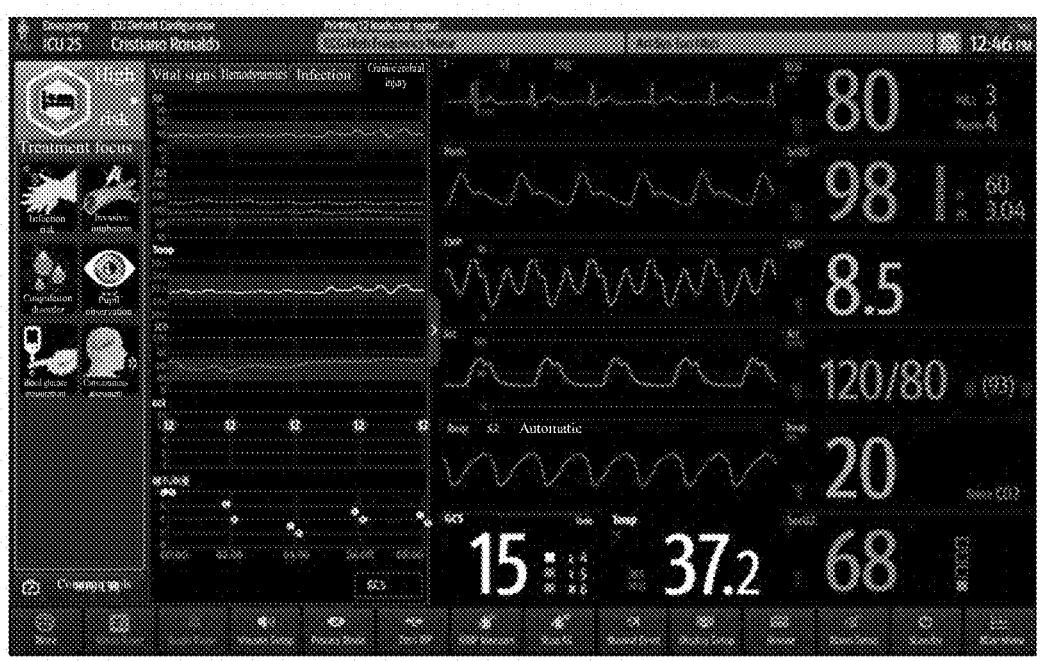
FIG. 11e is another schematic diagram of a main monitoring interface in an embodiment of the disclosure.

The medical device may also receive operation instructions for displaying other options from the user, and display, according to the operation instructions, physiological sign trend waveform information and statistical analysis information of trend waveforms corresponding to the other options. As shown in FIG. 11c, physiological sign trend waveform information and statistical analysis information of trend waveforms of the monitored subject under a hemodynamic system option are displayed, and physiological sign trend waveform information associated with blood is mainly displayed. FIG. 11d shows physiological sign trend waveform information and statistical analysis information of trend waveforms of the monitored subject under an infection system option, and mainly shows a quick sequential organ failure assessment (qSOFA) score, where the qSOFA score is generated through statistical analysis of multiple kinds of value monitoring information. FIG. 11e shows physiological sign trend waveform information and statistical analysis information of trend waveforms of the monitored subject under a craniocerebral injury system option, including a Glasgow coma scale (GCS), pupil measurement data, etc.

In an embodiment of the disclosure, waveform monitoring information is displayed in the main monitoring interface of the medical device, and the displayed waveform monitoring information includes at least one of the value monitoring information, the physiological sign analog signal waveform information, the physiological sign trend waveform information or the statistical analysis information of trend waveforms. The physiological sign trend waveform information and the statistical analysis information of trend waveforms under different physiological systems of the monitored subject may also be displayed according to the actual requirements of the user. The convenience of the user in operating the medical advice tools and acquiring monitoring data of the monitored subject is further improved.

A monitoring device of the disclosure is described in detail below.

Figure 10A:
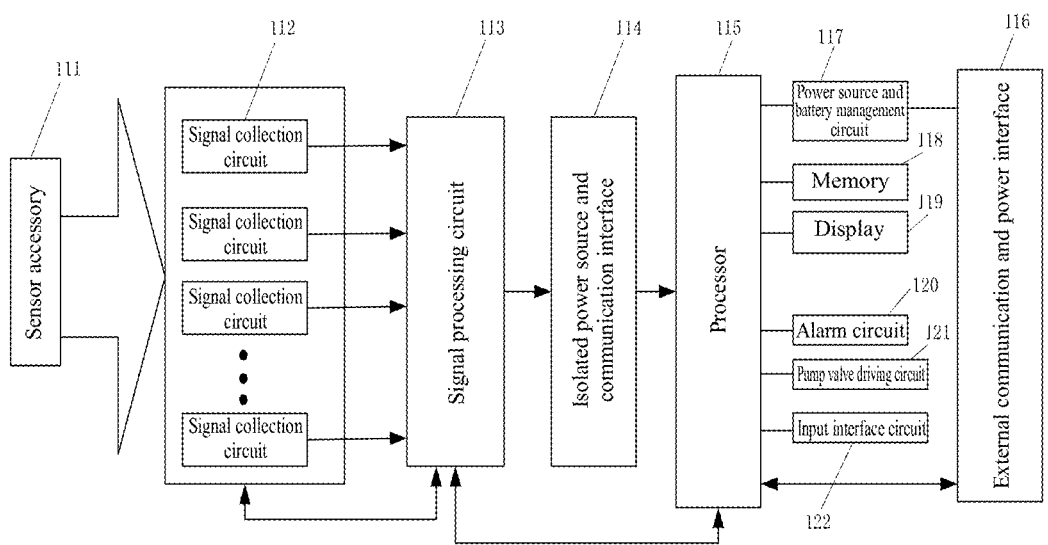
FIG. 10a is a structural schematic diagram of a monitoring device.

Referring to FIG. 10, the monitoring device has an independent housing, and a housing panel has a sensor interface area, in which a plurality of sensor interfaces are integrated and configured to be connected to various external physiological parameter sensor accessories 111. The housing panel further includes a small display area, a display 119, an input interface circuit 122, a power source and battery management circuit 117, a memory 118, a pump and valve driving circuit 121, an alarm circuit 120 (such as an LED alarm area), etc. A parameter processing module is used as an external communication and power interface for communicating with a host and taking power from the host. The parameter processing module also supports a build-out parameter module, may form a plug-in monitoring device host by means of inserting a parameter module, may be used as part of the monitoring device, or may be connected to the host via a cable, with the build-out parameter module being used as an external accessory of the monitoring device.

An internal circuit of the parameter processing module is disposed in the housing. As shown in FIG. 9, the internal circuit includes signal collection circuits 112 corresponding to at least two physiological parameters, a front-end signal processing circuit 113, and a processor 115. The signal collection circuit 112 may be selected from an electrocardiogram circuit, a respiration circuit, a body temperature circuit, a blood oxygen circuit, a non-invasive blood pressure circuit, an invasive blood pressure circuit, etc. These signal collection circuits 112 are respectively electrically connected to corresponding sensor interfaces, so as to be electrically connected to the sensor accessories 111 corresponding to different physiological parameters. An output end of the signal collection circuit is coupled to a front-end signal processor, a communication port of the front-end signal processor is coupled to the processor, and the processor is electrically connected to the external communication and power interface by means of the power source and battery management circuit 117. Various physiological parameter measurement circuits can use common circuits in the prior art. The front-end signal processor completes sampling and analog-to-digital conversion of an output signal of the signal collection circuit, and outputs a control signal to control a measurement process of the physiological signal. These parameters include but are not limited to: parameters such as electrocardiogram, respiration, body temperature, blood oxygen, non-invasive blood pressure, and invasive blood pressure. The front-end signal processor may be implemented using a single chip microcomputer or other semiconductor devices. The front-end signal processor may be powered by an isolated power source. The sampled data is simply processed and packaged, and then sent to the processor by means of an isolated communication interface. For example, the front-end signal processor circuit may be coupled to the processor 115 by means of the isolated power source and the communication interface 114. The reason that the front-end signal processor is powered by the isolated power source is that a DC/DC power source isolated by a transformer plays a role in isolating the patient from a power supply device, and the main purposes are: 1. isolating the patient, and enabling a disclosure part to be floating by means of the isolation transformer, so that a leakage current of the patient is small enough; and 2. preventing the voltage or energy during defibrillation or electrotome application from affecting a board card and a device of an intermediate circuit such as a main control board (guaranteed by a creepage distance and an electrical clearance). The processor completes the calculation of the physiological parameters, and sends calculation results and waveforms of the parameters to the host (such as a host with a display, a PC, and a central station) by means of the external communication and power interface. The external communication and power interface 116 may be one or a combination of local area network interfaces composed of Ethernet, a token ring, a token bus, and an optical fiber distributed data interface (FDDI) as the backbone of these three networks, may also be one or a combination of wireless interfaces such as infrared, Bluetooth, Wifi, and WMTS communication, or may also be one or a combination of wired data connection interfaces such as RS232 and USB. The external communication and power interface 116 may also be one of a wireless data transmission interface and a wired data transmission interface or a combination thereof. The host may be any computer device such as a host of a monitoring device, an electrocardiograph, an ultrasonic diagnosis instrument, and a computer, and a monitoring device can be formed by means of installing matching software. The host may further be a communication device such as a mobile phone, and the parameter processing module sends, by means of a Bluetooth interface, data to the mobile phone supporting Bluetooth communication, so as to implement remote transmission of the data.

Specifically, the display 119 is used for configuring display information according to instructions of the processor 115.

The processor 115 executes program instructions to implement the following steps: displaying a medical advice setup area in a display interface of the monitoring device at a first moment; and displaying criticality level information and/or medical advice information of a monitored subject in the medical advice setup area at a second moment, where the second moment is later than the first moment.

In an embodiment, the processor 115 is configured to: display physiological state information of the monitored subject associated with the criticality level information and/or the medical advice information in the display interface at a third moment, where the third moment is later than the second moment.

In an embodiment, the processor 115 is configured to: receive a display setup instruction; display a setup interface in the display interface in response to the display setup instruction, where the setup interface includes at least one of a criticality setup interface, a state setup interface and an operation setup interface; and receive the criticality level information and/or the medical advice information input by a user on the setup interface.

In an embodiment, the criticality setup interface includes at least two criticality level options; the state setup interface includes at least one of a blood coagulation disorder option, an invasive intubation option, a postoperative flat lying option, or an infection risk option; and the operation setup interface includes at least one of operation options of blood glucose monitoring, consciousness evaluation, blood gas analysis, or pupil observation.

In an embodiment, the processor 115 is configured to: acquire basic physiological parameter information of the monitored subject, and the physiological state information includes the basic physiological parameter information.

In an embodiment, the processor 115 is configured to: receive a function display instruction; and display a medical advice tool interface in the display interface in response to the function display instruction.

In an embodiment, the processor 115 is configured to: receive monitoring information of at least one physiological parameter that is indicated by the criticality level information and/or the medical advice information and is input by the user on the medical advice tool interface, and the physiological state information includes the monitoring information of the at least one physiological parameter indicated by the criticality level information and/or the medical advice information.

In an embodiment, the processor 115 is configured to: display a target area in the display interface; and display monitoring information of at least one physiological parameter indicated by the criticality level information and/or the medical advice information in the target area.

In an embodiment, the processor 115 is configured to: display at least one of an operation standard, an operation mode or an information entry prompt on the medical advice tool interface, where the operation standard is used for indicating requirements to a user role for a medical operation on the monitored subject, the operation mode is used for indicating steps of a medical operation performed on the monitored subject by the user role, and the information entry prompt is used for prompting the user role to input measurement information associated with the monitored subject.

In an embodiment, the processor 115 is configured to: display timing information in the medical advice display area at a second moment; and give a prompt if a timing in the timing information is finished.

The processor 115 executes program instructions to implement the following steps: displaying a medical advice setup area in a display interface of the monitoring device; acquiring a first operation instruction; and displaying criticality level information and/or medical advice information of a monitored subject in the medical advice setup area in response to the first operation instruction.

In an embodiment, the processor 115 is configured to: acquire a second operation instruction; and display a medical advice tool interface in the display interface in response to the second operation instruction.

In an embodiment, the processor 115 is configured to: acquire a third operation instruction; and display physiological state information of the monitored subject associated with the criticality level information and/or the medical advice information in the display interface in response to the third operation instruction.

In an embodiment, the first operation instruction is input by a first user role, the second operation instruction and the third operation instruction are input by a second user role, the first user role includes a doctor, and the second user role includes a nurse.

In an embodiment, the processor 115 is configured to: receive the third operation instruction input by the second user role on the medical advice tool interface; displaying a target area in the display interface; and displaying monitoring information of at least one physiological parameter indicated by the criticality level information and/or the medical advice information in the target area.

In an embodiment, the processor 115 is configured to: display at least one of an operation standard, an operation mode or an information entry prompt on the medical advice tool interface, where the operation standard is used for indicating requirements of the second user role for a medical operation on the monitored subject, the operation mode is used for indicating steps of a medical operation performed on the monitored subject by the second user role, and the information entry prompt is used for prompting the second user role to input measurement information associated with the monitored subject.

In an embodiment, the processor 115 is configured to: receive a display setup instruction triggered by the first user role in the medical advice setup area; display a setup interface in the display interface in response to the display setup instruction, where the setup interface includes at least one of a criticality setup interface, a state setup interface or an operation setup interface; and receive the first operation instruction input by the first user role on the setup interface.

In an embodiment, the criticality setup interface includes at least two criticality level options; the state setup interface includes at least one of a blood coagulation disorder option, an invasive intubation option, a postoperative flat lying option, or an infection risk option; and the operation setup interface includes at least one of operation options of blood glucose monitoring, consciousness evaluation, blood gas analysis, or pupil observation.

In an embodiment, the processor 115 is configured to: display timing information in the medical advice display area in response to the first operation instruction; and give a prompt if a timing in the timing information is finished.

In an embodiment, the processor 115 is configured to: send the physiological state information of the monitored subject to an external device, where the external device includes at least one of a central station, a mobile terminal or a computerized medical record system.

Figure 10B:
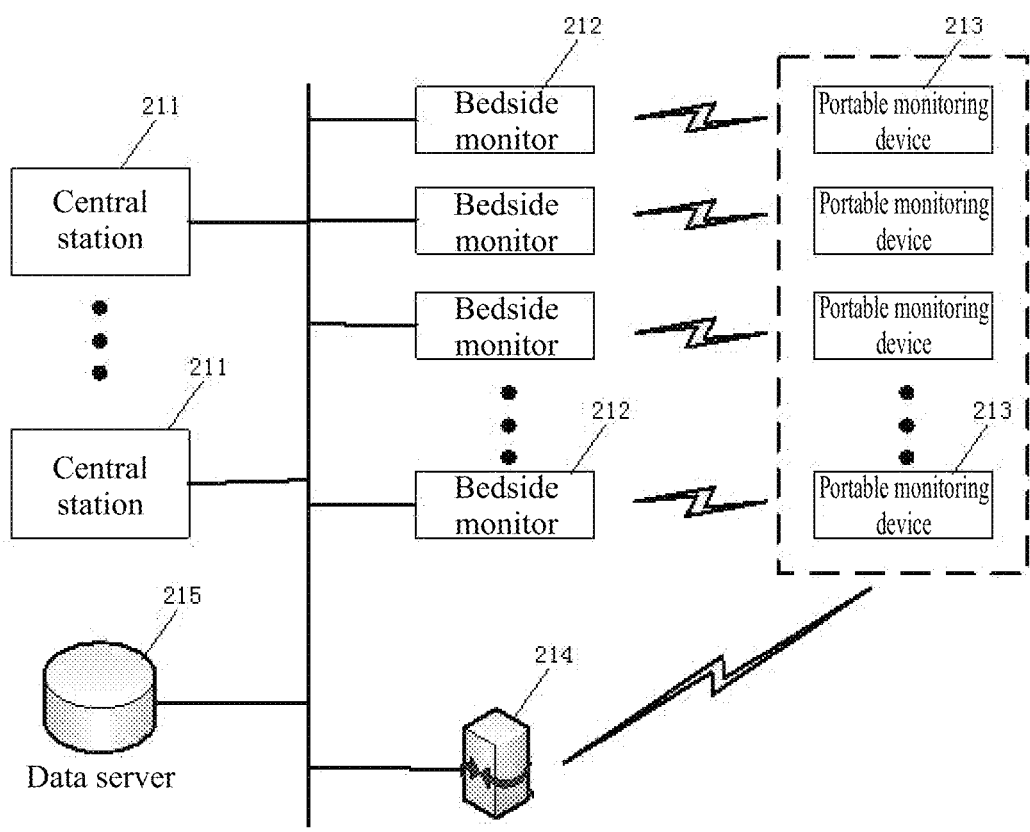
FIG. 10b is a schematic diagram of a medical device networking system in an embodiment of the disclosure.

As shown in FIG. 10b, a medical device networking system used in a hospital is provided. By using the system, data of the medical device may be saved as a whole to centrally manage patient information and nursing information that are stored in association, which facilitates storage of historical data and alarming in association. In the system shown in FIG. 10b, a bedside medical device 212 may be provided for each hospital bed. The bedside medical device 212 may be the multi-parameter medical device or plug-in medical device as described above. In addition, each bedside medical device 212 may further be paired with a portable monitoring device 213 for transmission. The portable monitoring device 213 provides a simple and portable parameter processing module which may be worn on the body of a patient to perform mobile monitoring for the patient. After the portable monitoring device 213 and the bedside medical device 212 perform wired or wireless communication, physiological data generated through mobile monitoring may be transmitted to the bedside medical device 212 for display, or transmitted, by means of the bedside medical device 212, to a central station 211 for a doctor or a nurse to view, or transmitted, by means of the bedside medical device 212, to a data server 215 for storage. In addition, the portable monitoring device 213 may further directly transmit, by means of a wireless network node 214 disposed in the hospital, the physiological data generated through mobile monitoring to the central station 211 for storage and display, or transmit, by means of the wireless network node 214 disposed in the hospital, the physiological data generated through mobile monitoring to the data server 215 for storage. It can be seen that the data corresponding to the physiological parameters displayed on the bedside medical device 212 may originate from a sensor accessory directly connected to a monitor, or from the portable monitoring device 213, or from the data server.

Those skilled in the art would have clearly understood that for convenience and conciseness of description, the specific working processes of the above-described systems, devices and units can refer to the corresponding processes in the above-described embodiments of the method and will not be further described here.

In several embodiments provided in the disclosure, it should be understood that the disclosed systems, apparatuses and methods may be implemented in other ways. For example, the apparatus embodiments described above are merely exemplary. For example, the division of units is only a logic function division. In actual implementation, there may be other division methods, for example, multiple units or components may be combined or integrated into another system, or some features may be omitted or not implemented. In a further aspect, the mutual coupling or direct coupling or communication connection shown or discussed may be indirect coupling or communication connection through some interfaces, apparatuses or units, and may be in electrical, mechanical or other forms.

The units described as separate parts may or may not be physically separated, and the parts displayed as units may or may not be physical units, that is, may be located in one place or may be distributed over multiple network units. Some or all of the units can be selected according to actual needs to achieve the objectives of solutions of the embodiments.

Additionally, the functional units in the embodiments of the disclosure may be integrated into one processing unit or may exist as being physically separate, or two or more of the units may be integrated into one unit. The above integrated unit may be implemented in the form of hardware or a software function unit.

If the integrated unit is implemented in the form of the software function unit and sold or used as an independent product, it may be stored in a computer-readable storage medium. Based on such an understanding, the technical solution of the disclosure essentially, or a part contributing to the prior art, or all or part of the technical solution may be embodied in the form of a software product. The computer software product is stored in a storage medium and comprises several instructions to cause a computer device (which may be a personal computer, a server, a network device, etc.) to execute all or some steps of the method described in the embodiments of the disclosure. The foregoing storage medium includes: a USB disk, a mobile hard disk, a Read-Only Memory (ROM), a Random Access Memory (RAM), a magnetic disk, or an optical disk, and other media that can store program codes.

As described above, the above embodiments are merely used for illustrating rather than limiting the technical solution of the disclosure. Although the disclosure has been illustrated in detail with reference to the foregoing embodiments, it should be understood by those of ordinary skill in the art that modifications can still be made to the technical solution described in the foregoing embodiments or equivalent substitutions of some technical features thereof is also possible, while these modifications or substitutions do not make the essence of the corresponding technical solution depart from the spirit and scope of the technical solutions of the embodiments of the disclosure.

What is claimed is:

1. A monitoring device, comprising:
a display configured to display information; and
a processor configured to:
display a medical advice setup area in a display interface of the monitoring device;
acquire a first operation instruction input by a first user role on a setup interface separate from the medical advice setup area; display at least one of criticality level in or medical advice information of a monitored subject in the medical advice setup area in response to the first operation instruction;
acquire a second operation instruction; and display a medical advice tool interface in the display interface in response to the second operation instruction; and
acquire a third operation instruction; and display physiological state information of the monitored subject associated with at least one of the criticality level information or the medical advice information in the display interface in response to the third operation instruction;
wherein the first operation instruction is input by the first user role, the second operation instruction and the third operation instruction are input by a second user role, the first user role comprises a doctor, and the second user role comprises a nurse,
wherein the processor is further configured to:
receive a display setup instruction triggered by the first user role in the medical advice setup area;
display the setup interface in the display interface separate from the medical advice setup area in response to the display setup instruction, wherein the setup interface comprises at least one of a criticality setup interface, a state setup interface or an operation setup interface;
receive the first operation instruction input by the first user role on the setup interface; and
hide the setup interface and display the criticality level information or the medical advice information in the medical advice setup area.

2. The monitoring device of claim 1, wherein
the criticality setup interface comprises at least two criticality level options;
the state setup interface comprises at least one of a blood coagulation disorder option, an invasive intubation option, a postoperative flat lying option, or an infection risk option; and
the operation setup interface comprises at least one of operation options of blood glucose monitoring, consciousness evaluation, blood gas analysis, or pupil observation.

3. The monitoring device of claim 1, wherein the processor is further configured to:
display timing information in the medical advice display area in response to the first operation instruction; and
give a prompt if a timing in the timing information is finished.

4. The monitoring device of claim 1, wherein the processor is further configured to:
receive the third operation instruction input by the second user role on the medical advice tool interface;
display a target area in the display interface; and
display monitoring information of at least one physiological parameter indicated by at least one of the criticality level information or the medical advice information in the target area.

5. The monitoring device of claim 1, wherein the processor is further configured to:
display at least one of an operation standard, an operation mode or an information entry prompt on the medical advice tool interface, wherein the operation standard is used for indicating requirements to the second user role for a medical operation on the monitored subject, the operation mode is used for indicating steps of a medical operation performed on the monitored subject by the second user role, and the information entry prompt is used for prompting the second user role to input measurement information associated with the monitored subject.

* * * * *